(12) United States Patent
Miura

(10) Patent No.: US 7,458,970 B2
(45) Date of Patent: Dec. 2, 2008

(54) HEATING TREATMENT APPARATUS

(75) Inventor: Keisuke Miura, Hachioji (JP)

(73) Assignee: Olympus Corporation, Tokyo (JP)

( * ) Notice: Subject to any disclaimer, the term of this patent is extended or adjusted under 35 U.S.C. 154(b) by 286 days.

(21) Appl. No.: 10/690,300

(22) Filed: Oct. 21, 2003

(65) Prior Publication Data
US 2004/0082971 A1 Apr. 29, 2004

(30) Foreign Application Priority Data
Oct. 25, 2002 (JP) ............................. 2002-311599
Sep. 2, 2003 (JP) ............................. 2003-310628

(51) Int. Cl.
*A61B 18/18* (2006.01)
(52) U.S. Cl. ...................................... 606/27
(58) Field of Classification Search ............ 606/1, 606/27–52; 607/3; 600/411, 439
See application file for complete search history.

(56) References Cited

U.S. PATENT DOCUMENTS

| | | | |
|---|---|---|---|
| 3,826,263 A | 7/1974 | Cage et al. | |
| 4,719,919 A * | 1/1988 | Marchosky et al. | 607/113 |
| 6,165,169 A * | 12/2000 | Panescu et al. | 606/1 |
| 6,387,092 B1 * | 5/2002 | Burnside et al. | 606/32 |
| 6,695,837 B2 * | 2/2004 | Howell | 606/29 |

FOREIGN PATENT DOCUMENTS

JP 53-9031 4/1978

* cited by examiner

*Primary Examiner*—Roy D. Gibson
*Assistant Examiner*—Peter J Vrettakos
(74) *Attorney, Agent, or Firm*—Scully, Scott, Murphy & Presser, P.C.

(57) ABSTRACT

The heating treatment device according to the present invention is constituted by a coagulation and incision forceps having a plurality of built-in heating elements, and a device main unit. A forceps identifying section inside the device main unit recognizes the identification of the type of forceps by an identifier, and information for the individual heating elements, and supplies the same to a temperature control and correction section. The temperature control and correction section reads out from a memory the resistance values for controlling required for the respective set temperatures for the respective heating elements, on the basis of this information. A heating setting section sets a resistance value for controlling for the set temperature level, from these resistance values for controlling. The resistance value detecting section calculates the resistance value for the heating elements from the measurement results of an applied power detecting section. An output power control section controls the output of electrical power to the heating elements in such a manner that the resistance value thus calculated is maintained to be equal to the resistance value which is set by the heating setting section.

7 Claims, 16 Drawing Sheets

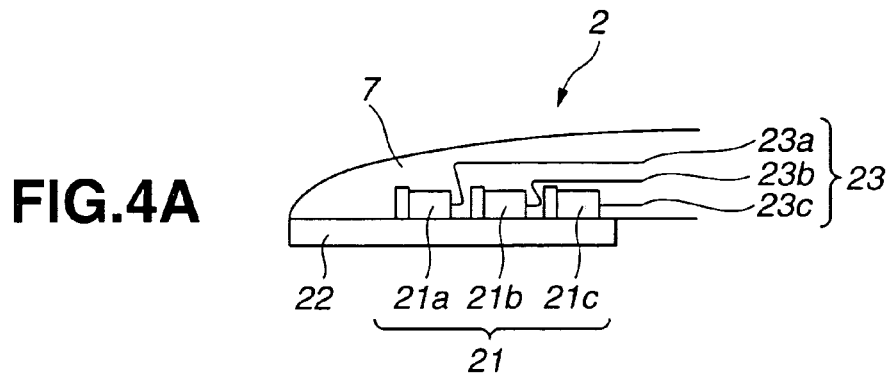
FIG.4A
FIG.4B
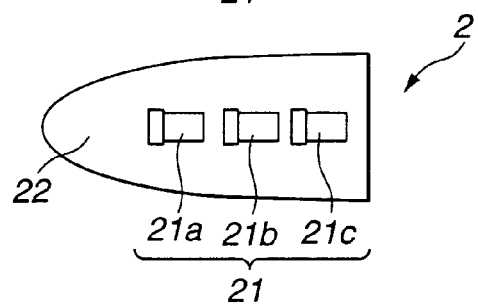
FIG.7
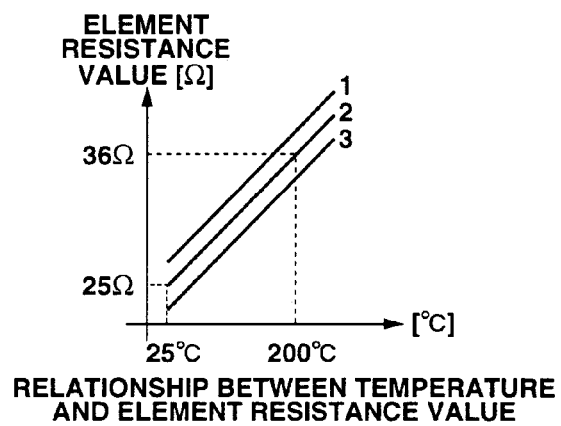
RELATIONSHIP BETWEEN TEMPERATURE
AND ELEMENT RESISTANCE VALUE
FIG.8
FORCEPS IDENTIFICATION TABLE
| FORCEPS TYPE | IDENTIFICATION GROUP NUMBER | NUMBER OF ELEMENTS | FORCEPS IDENTIFIER |
|---|---|---|---|
| TWEEZERS FORCEPS | A | 1 | 10kΩ |
| FORCEPS FOR LAPAROSCOPIC SURGERY | B | 2 | 20kΩ |
| FORCEPS FOR SURGERY | C | 3 | 30kΩ |

FIG.9

CLASSIFICATION OF HEATING ELEMENT GROUPS
IN ACCORDANCE WITH HEATING ELEMENT INITIAL
CHARACTERISTICS (INITIAL RESISTANCE VALUE)

| INITIAL CHARACTERISTICS OF HEATING ELEMENT (RANGE OF INITIAL RESISTANCE VALUE) | IDENTIFICATION GROUP NUMBER | HEATING ELEMENT IDENTIFIER 10b |
|---|---|---|
| 26±0.5Ω | 1 | 10kΩ |
| 25±0.5Ω | 2 | 20kΩ |
| 24±0.5Ω | 3 | 30kΩ |

FIG.10

TABLE : SET TEMPERATURE RESISTANCE VALUE
FOR CONTROLLING HEATING ELEMENT (IN MEMORY 40)

| SET LEVEL | RESISTANCE VALUE FOR CONTROLLING HEATING ELEMENT [Ω] | | |
|---|---|---|---|
| | "HEATING ELEMENT INITIAL CHARACTERISTICS" IDENTIFICATION GROUP NUMBER | | |
| | 1 | 2 | 3 |
| 1 (180°C) | 32 | 31 | 30 |
| 2 (190°C) | 34 | 33 | 32 |
| 3 (200°C) | 36 | 35 | 34 |
| 4 (210°C) | 38 | 37 | 36 |
| 5 (220°C) | 40 | 39 | 38 |

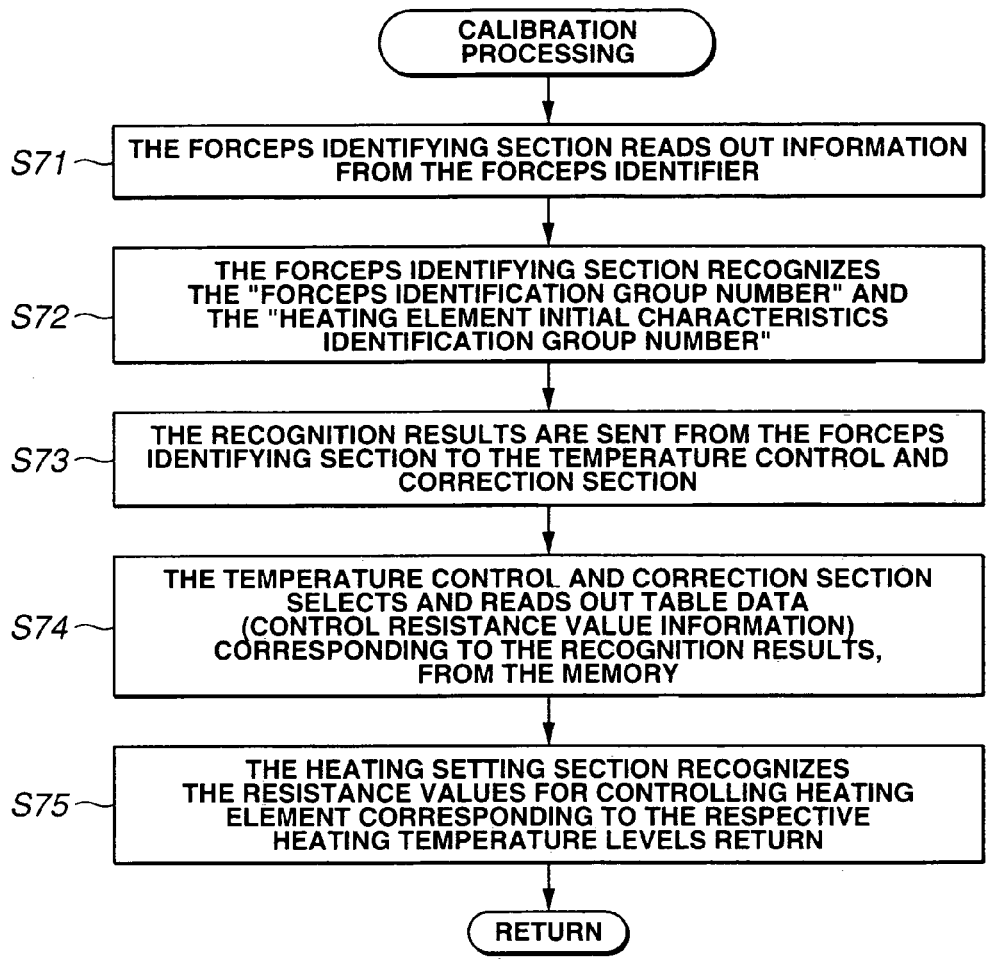
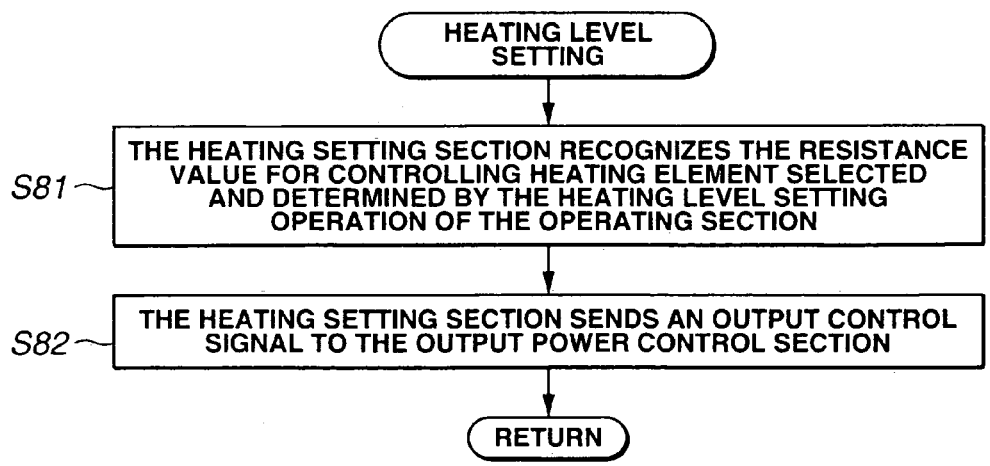

FIG.15

CLASSIFICATION OF HEATING PATTERN GROUPS
IN ACCORDANCE WITH HEATING PATTERN INITIAL
CHARACTERISTICS (INITIAL RESISTANCE VALUE)

| INITIAL CHARACTERISTICS OF HEATING PATTERN (RANGE OF INITIAL RESISTANCE VALUE) | IDENTIFICATION GROUP NUMBER | HEATING PATTERN IDENTIFIER 50b-1, 50b-2, 50b-3 |
|---|---|---|
| 26±0.5Ω | 1 | 10kΩ |
| 25±0.5Ω | 2 | 20kΩ |
| 24±0.5Ω | 3 | 30kΩ |

FIG.16

IDENTIFICATION GROUP NUMBER ACCORDING TO INITIAL
CHARACTERISTICS OF EACH HEATING PATTERN

| HEATING PATTERN IDENTIFIER | 50b-1 | 50b-2 | 50b-3 |
|---|---|---|---|
| IDENTIFICATION GROUP NUMBER | 2 | 1 | 3 |

FIG.17

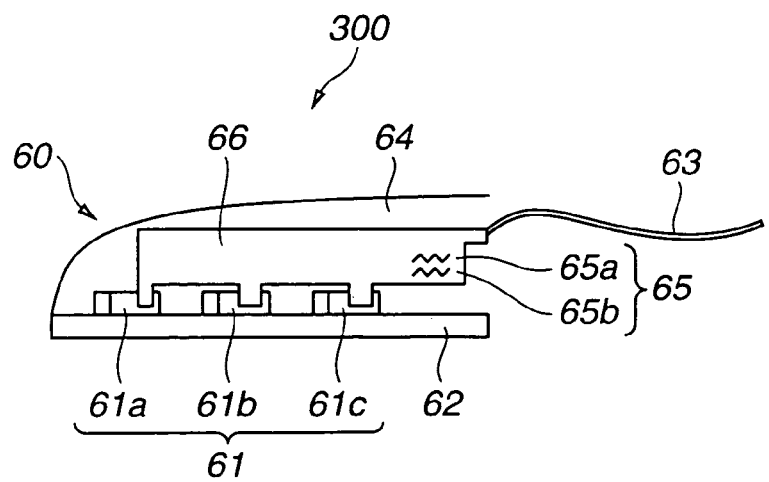

TABLE : RESISTANCE VALUE FOR CONTROLLING HEATING ELEMENT CALCULATION RESULTS

| SET LEVEL | RESISTANCE VALUE FOR CONTROLLING HEATING ELEMENT (Ω) | | |
| --- | --- | --- | --- |
| | HEATING ELEMENT TYPE | | |
| | HEATING ELEMENT 21a | HEATING ELEMENT 21b | HEATING ELEMENT 21c |
| 1(180°C) | 30 | 31 | 32 |
| 2(190°C) | 32 | 33 | 34 |
| 3(200°C) | 34 | 35 | 36 |
| 4(210°C) | 36 | 37 | 38 |
| 5(220°C) | 38 | 39 | 40 |

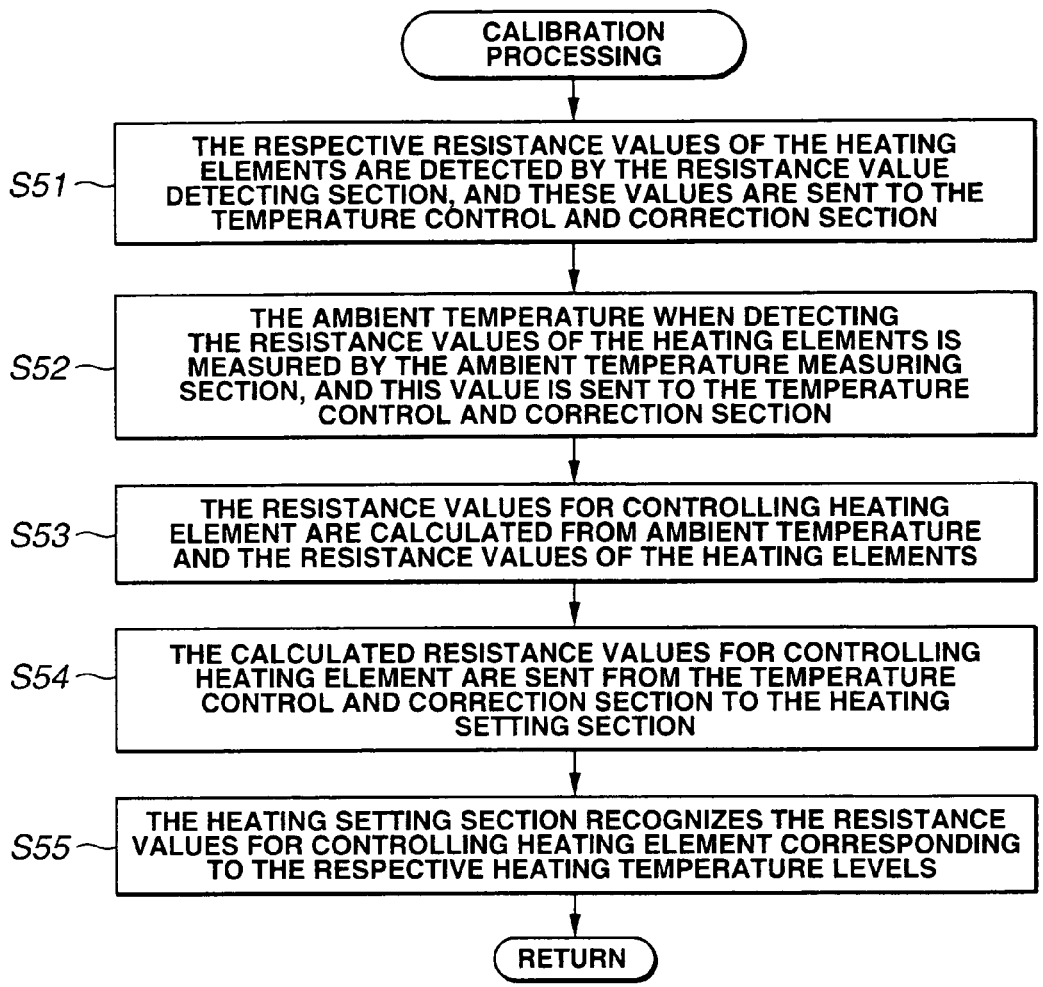
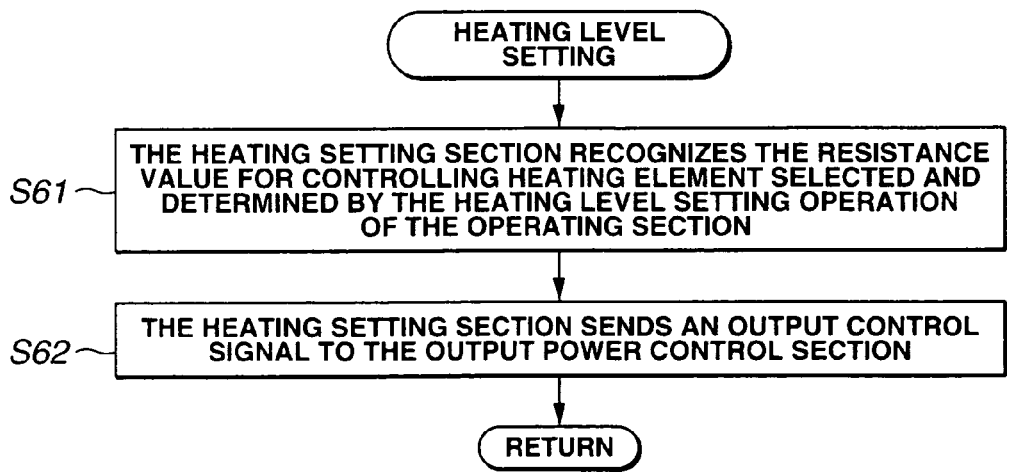

US 7,458,970 B2

HEATING TREATMENT APPARATUS

This application claims benefit of Japanese Application No. 2002-311599 filed in Japan on Oct. 25, 2002 and No. 2003-310628 filed in Japan on Sep. 2, 2003, the contents of which are incorporated by this reference.

BACKGROUND OF THE INVENTION

1. Field of the Invention

The present invention relates to a heating treatment device and a heating operation control method therefor, and more particularly to a heating treatment device and heating operation control method for treating an affected area by applying heat thereto.

2. Description of the Related Art

In general, a heating treatment device is used in surgical operation or internal operation when carrying out procedures such as incision, coagulation, staunching, and the like. A heating treatment device comprises a treatment section on which there is provided a heating element, which is a heat generating section for heating the affected area, in such a manner that a treatment such as incision, coagulation, staunching, or the like, can be performed by applying heat generated by the heating element of the treatment section to the affected area.

In a heating treatment device of this kind, technology has been proposed wherein, by providing a treatment section having a plurality of heater segments divided as heating elements, the treatment section of the heating treatment device treats the affected area reliably by applying heat generated from the plurality of heater segments, which are set to the same temperature, to the affected area (for example, see Japanese Patent Laid-open No. 53-9031).

SUMMARY OF THE INVENTION

In summary, the heating treatment device according to the present invention comprises: a heater for generating heat for treating living-body tissue; a driving circuit for driving the heater; an initial characteristics judging device for judging the initial characteristics of the heater; and a calibration device for calibrating the driving circuit on the basis of the judgment results of the initial characteristics judging device.

The above and other objects, features and advantages of the invention will become more clearly understood from the following description referring to the accompanying drawings.

BRIEF DESCRIPTION OF THE DRAWINGS

FIG. 4A is a schematic diagram showing an overview of the heating treatment device in FIG. 3;

FIG. 4B is a schematic diagram of the heating treatment section in FIG. 4A as viewed from the upper position;

FIG. 7 is a graph showing the relationship between temperature and resistance value for the heating elements of the heating treatment device in FIG. 3;

FIG. 8 shows a table indicating types of forceps which are fitted to the main unit of the device in FIG. 2;

FIG. 9 shows a table indicating the initial characteristics of a heating element of the heating treatment section in FIG. 3;

FIG. 10 shows a table indicating the relationship between set temperatures and resistance values for controlling heating element;

FIG. 12 is a flowchart illustrating the calibration processing in FIG. 11;

FIG. 13 is a flowchart illustrating heat generation level setting in FIG. 11;

FIG. 15 is a diagram showing a table indicating group classifications according to initial characteristics of the heating patterns of the heating treatment section in FIG. 14;

FIG. 16 is a diagram showing a table indicating heating pattern identification group numbers according to the initial characteristics of the heating patterns of the heating treatment section in FIG. 14;

FIG. 17 is a diagram showing an overview of the composition of a heating treatment section of a heating treatment device illustrating a third embodiment of the present invention;

FIG. 23 is a flowchart illustrating the calibration processing in FIG. 22; and

FIG. 24 is a flowchart illustrating the heating level setting in FIG. 22.

DETAILED DESCRIPTION OF THE PREFERRED EMBODIMENTS

Below, embodiments of the present invention are described with reference to the drawings.

First Embodiment

Figure 1:
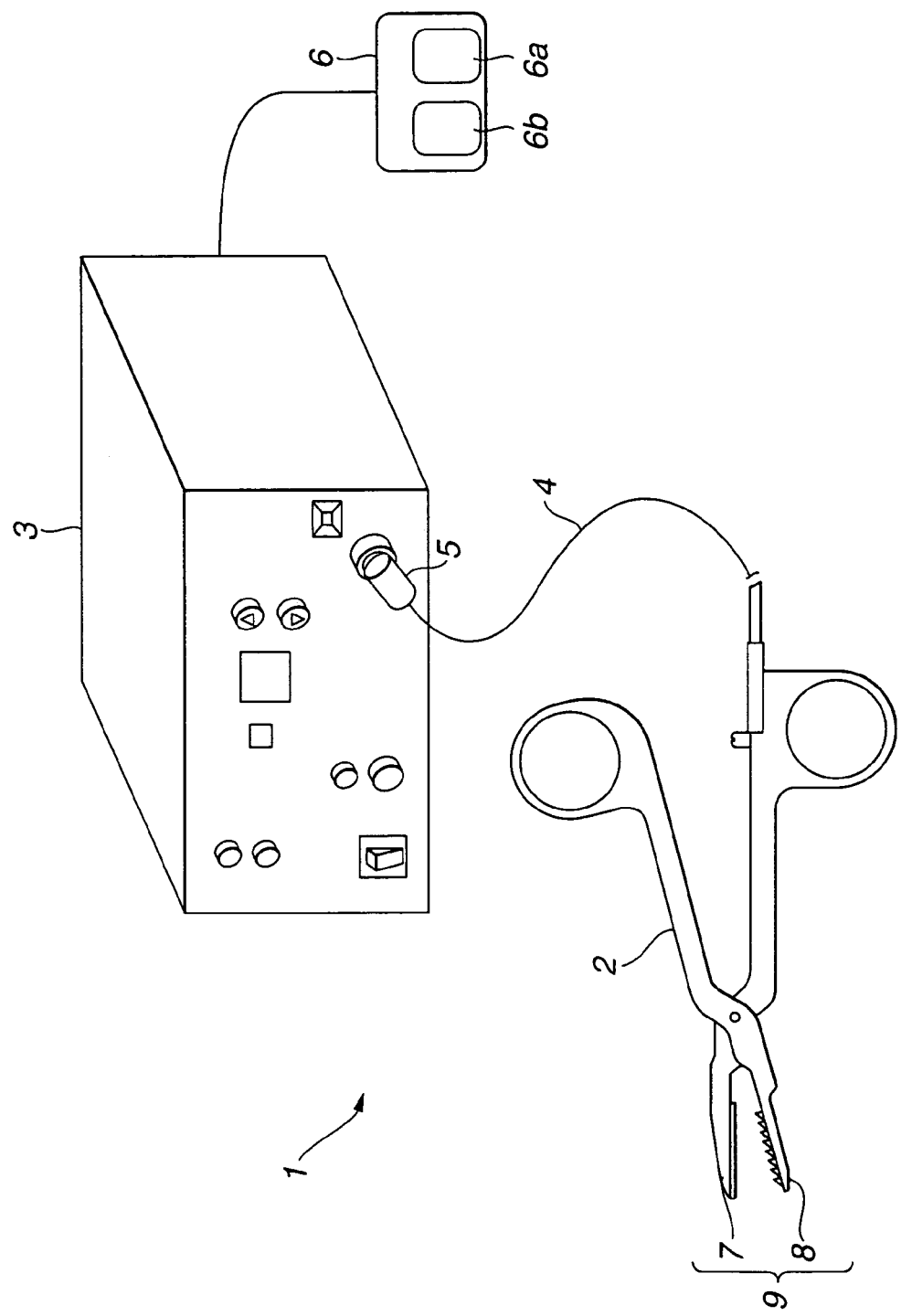
FIG. 1 is a perspective view of a heating treatment device showing a first embodiment of the present invention.
Figure 2A:
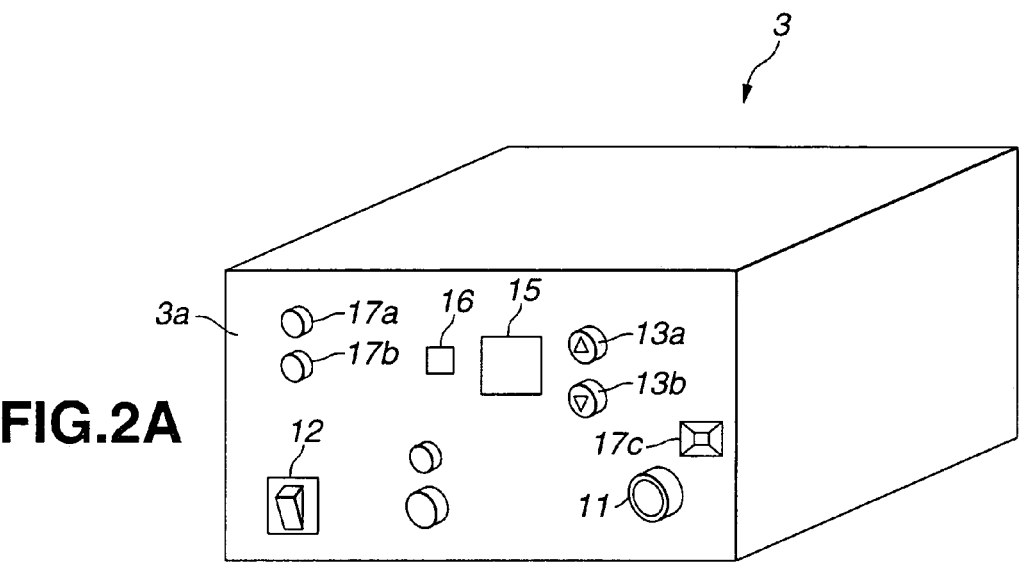
FIG. 2A is a perspective view of the main unit of the heating treatment device in FIG. 1 as viewed diagonally from front and upper right position.
Figure 2B:
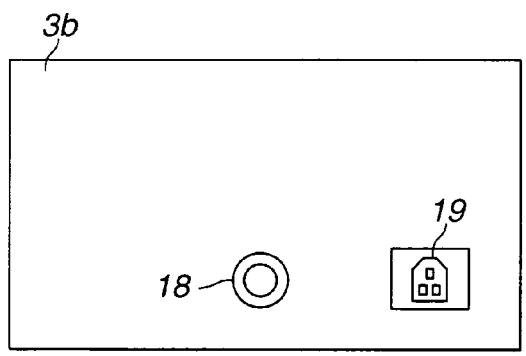
FIG. 2B is a rear view of the main unit of the device in FIG. 2A.
Figure 3:
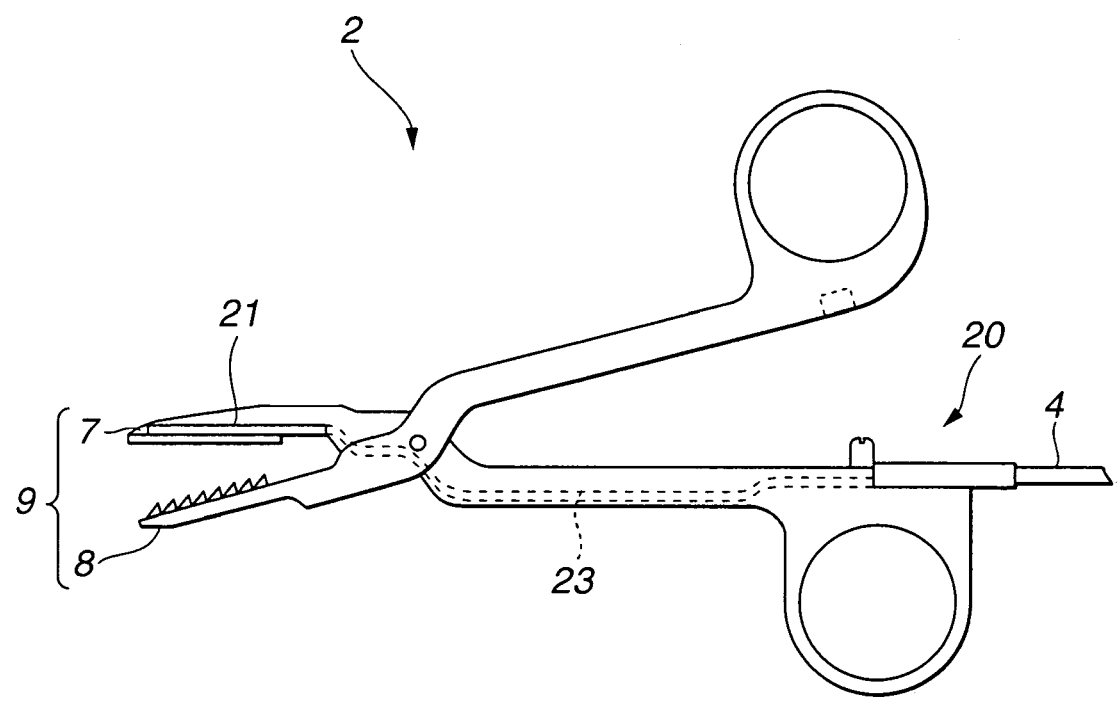
FIG. 3 is a perspective view showing a coagulation and incision forceps of the heating treatment device according to FIG. 1.
Figures 5A, 5B:
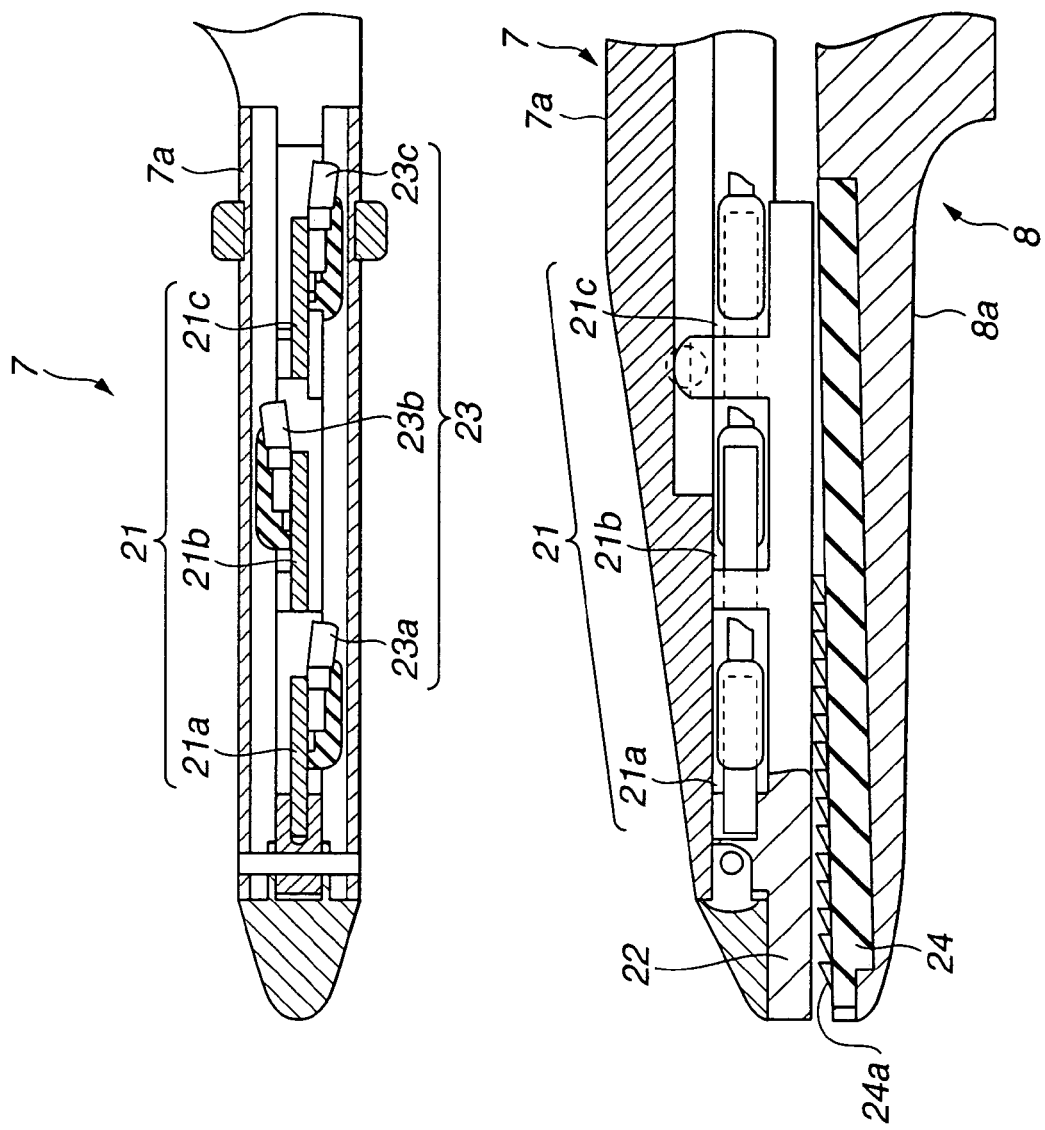
FIG. 5A is a sectional view of the heating treatment section in FIG. 3 as viewed from the upper position.
FIG. 5B is a longitudinal sectional view of the coagulation and incision forceps in FIG. 3.
Figure 6:
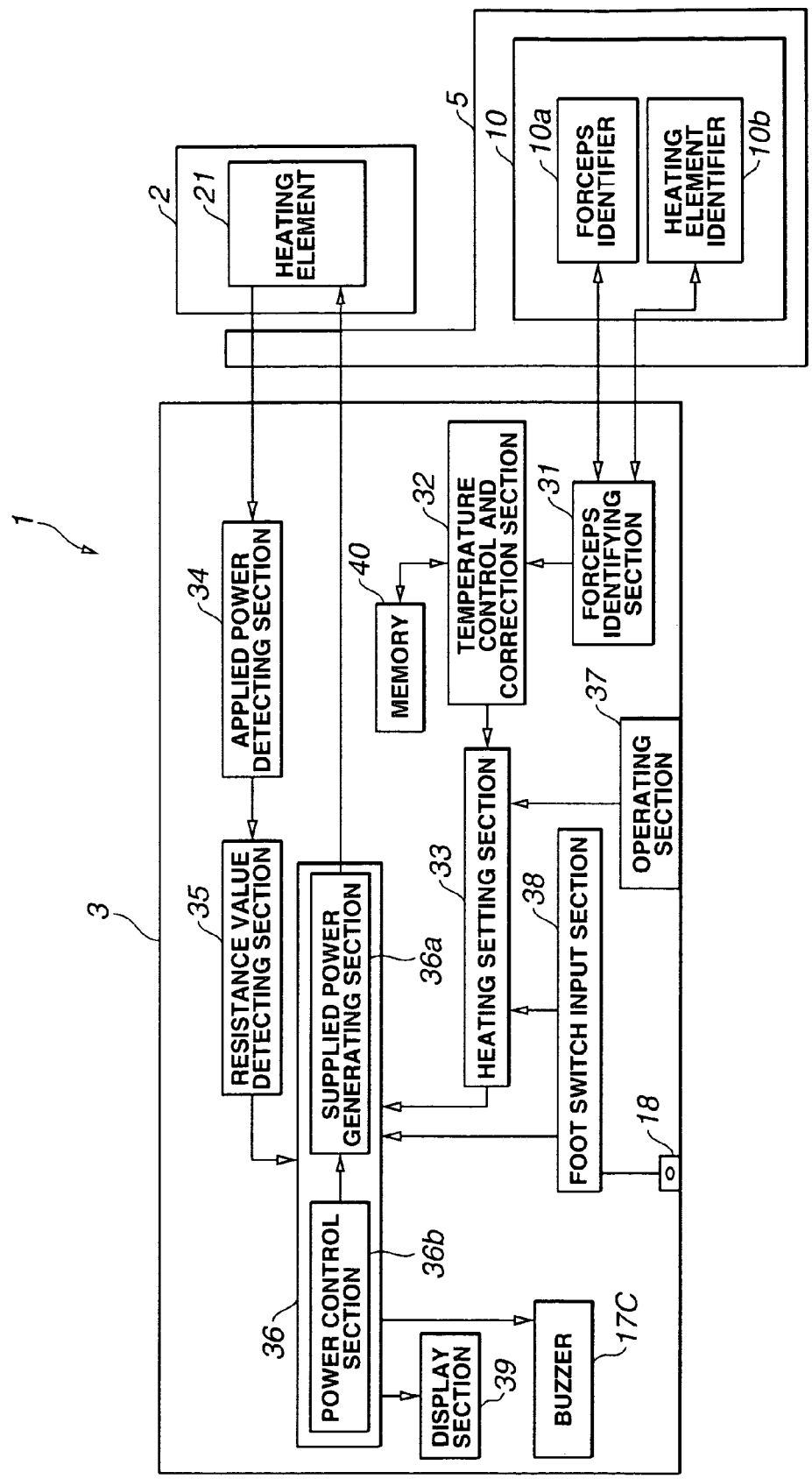
FIG. 6 is a block diagram showing the composition of an electrical circuit of a heating treatment device according to FIG. 1.
Figure 11:
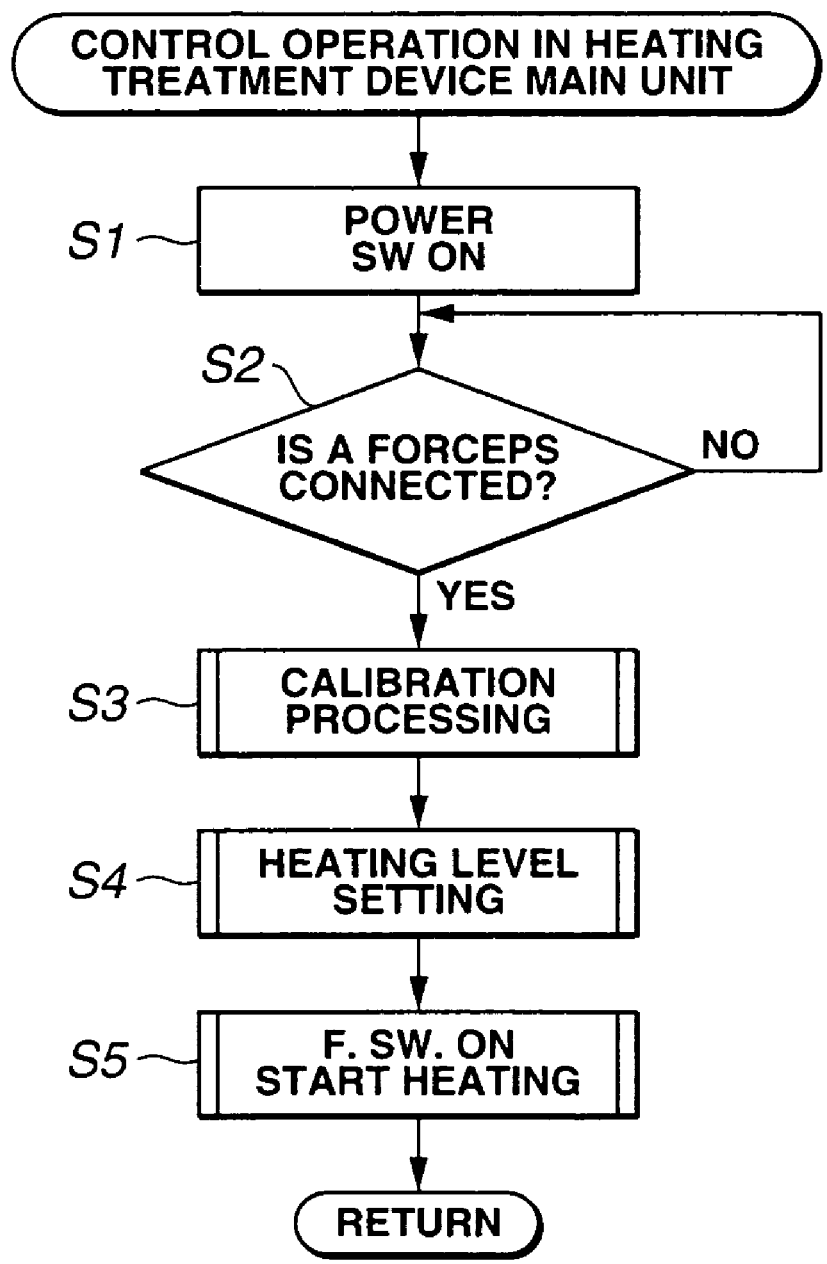
FIG. 11 is a flowchart showing a control operation for the device main unit of the heating treatment device in FIG. 1.

FIG. 1 to FIG. 13 relate to a first embodiment of a heating treatment device and a heating operation control method for the same, wherein FIG. 1 is a perspective view of a heating treatment device showing a first embodiment of the present invention; FIG. 2 shows an appearance of the main device body of the heating treatment device in FIG. 1, of which FIG. 2A is a perspective view of the main unit of the heating treatment device in FIG. 1 as viewed diagonally from front and upper right position and FIG. 2B is a rear view of the main unit of the device in FIG. 2A, FIG. 3 is a perspective view showing a coagulation and incision forceps of the heating treatment device according to FIG. 1; FIG. 4 shows diagrams illustrating the heating treatment section of the coagulation and incision forceps in FIG. 3, in which FIG. 4A is a schematic diagram showing an overview of the heating treatment device in FIG. 3, and FIG. 4B is a schematic diagram of the heating treatment section in FIG. 4A as viewed from the upper position; FIG. 5 shows diagrams illustrating the composition of the treatment section of the coagulation and incision forceps in FIG. 3, in which FIG. 5A is a top sectional view of the heating treatment section of the coagulation and incision forceps in FIG. 3 viewed in a vertical direction from the top thereof, and FIG. 5B is a side sectional view of the treatment section of the coagulation and incision forceps in FIG. 3 viewed in a horizontal direction from the side thereof; FIG. 6 is a block diagram showing the composition of an electrical circuit of a heating treatment device according to FIG. 1; FIG. 7 is a graph showing the relationship between temperature and resistance value for the heating element of the heating treatment device in FIG. 3; FIG. 8 shows a table indicating types of forceps which are fitted to the main unit of the device in FIG. 2 (where a plurality of types of treatment tools can be fitted to the main unit of the device); FIG. 9 shows a table indicating the initial characteristics of a heating element of the heating treatment section in FIG. 3; FIG. 10 shows a table, indicating the relationship between set temperatures and resistance values for controlling heating element control; FIG. 11 is a flowchart showing a control operation for the device main unit of the heating treatment device in FIG. 1; FIG. 12 is a flowchart illustrating calibration processing in FIG. 11, and FIG. 13 is a flowchart illustrating heat generation level setting in FIG. 11.

As shown in FIG. 1, the principal part of the heating treatment device 1 comprises a coagulation and incision forceps 2, which is a treatment tool constituting a built-in heating element 21 (see FIG. 4A, FIG. 4B), which will be described later, and a device main unit 3 in which the coagulation and incision forceps 2 is detachably provided, the device main unit 3 being a drive unit for driving and controlling the heating element of the coagulation and incision forceps 2 by supplying electrical power to the same.

A foot switch 6 is connected to the device main unit 3. The foot switch 6 comprises two switches, namely, a maximum temperature level output switch 6a and a set temperature level output switch 6b.

The coagulation and incision forceps 2 comprises a connection cable 4, and is connected freely detachably to the device main unit 3 by means of a main unit connector 5 provided on the other end of the connection cable 4. The coagulation and incision forceps 2 has a treatment section 9 which serves to grasp and treat living-body tissue, and the principal part of this treatment section 9 comprises a heating treatment section 7 having a plurality of heating elements and an elastic receiving section 8 which can be placed in contact with, and separated from, this heating treatment section 7.

When living-body tissue is grasped between the heating treatment section 7 and the elastic receiving section 8 of the treatment section 9 and the heating treatment section 7 is caused to generate heat by means of current being passed from the device main unit 3, the living-body tissue being grasped can be coagulated and cut. Moreover, since the number of heating elements 21 in the heating treatment section 7 differs according to the type of forceps, in response to the objective of the treatment, an identifier 10, which is an identification device for indicating the type of forceps, is built into the main unit connector 5 as shown in FIG. 6.

The identifier 10 comprises a forceps identifier 10a for indicating the type of forceps and a heating element identifier 10b for holding information relating to individual heating elements as shown in FIG. 6. The identifier 10 is, for example, an electrical resistance element, or a non-volatile memory in which identification information has been stored previously.

Moreover, as shown in FIG. 2A and FIG. 2B, the device main unit 3 comprises a front face panel 3a and a rear face panel 3b.

As shown in FIG. 2A, the front face panel 3a is provided with a connector receiving section 11 composed such that the main unit connector 5 of the connection cable 4 of the coagulation and incision forceps 2 can be freely attached thereto and detached therefrom.

The front face panel 3a has a power switch 12 for switching the power supply on and off, and a temperature level UP switch 13a and temperature level DOWN switch 13b for setting the heating temperature level of the heating treatment section 7 of the coagulation and incision forceps 2 to level 1 to 5.

Furthermore, the front face panel 3a also has a temperature level display LED 15 for indicating the temperature level set by the temperature level UP switch 13a and the temperature level DOWN switch 13b, an output display LED 16 for indicating that the heating elements of the coagulation and incision forceps 2 are being electrically conducted on, a forceps abnormality indicator LED 17a which flashes on and off in the event of an abnormality in the coagulation and incision forceps 2, a power supply abnormality indicator LED 17b which flashes on and off in the event of an abnormality in the internal circuitry of the device main unit 3, and a buzzer 17c which generates a warning sound.

On the other hand, the rear face panel 3b comprises a foot switch connector receiving section 18 and a power supply inlet 19, as illustrated in FIG. 2B. The device main unit 3 according to the present embodiment can be connected to a coagulation and incision forceps 2 having a maximum of four built-in heating elements, for example.

As shown in FIG. 3, as principal parts, the coagulation and incision forceps 2 comprises a treatment section 9 having a heating treatment section 7 and an elastic receiving section 8, as described above, and a handle section 20 for performing opening and closing operations in order to grasp living-body tissue by means of the treatment section 9. Moreover, one end of the connection cable 4 is connected to a coaxial lead wire 23 of the handle section 20, as described hereinafter.

As shown in FIG. 4A and FIG. 4B, in the heating treatment section 7 of the coagulation and incision forceps 2, a plurality of heating elements 21, constituting heaters, for example, three similar heating elements 21a, 21b, 21c, are arranged on a heat transfer plate 22 in a thermally coupled fashion.

A characteristic feature of the heating treatment device 1 according to the present embodiment lies in the fact that it is composed in such a manner that temperature irregularities in the heating treatment section 7 are reduced by performing output-control in response to the initial characteristics of the heating elements 21a, 21b, 21c.

Next, the structure of the treatment section 9 comprising a heating treatment section 7 and an elastic receiving section 8 will now be described with reference to FIG. 5A and FIG. 5B.

As shown in FIG. 5A and FIG. 5B, the heating treatment section 7 comprises heating elements 21 (21a to 21c) built into a heating treatment section main unit 7a.

Here, a "heating element" is a thin film resistor formed on a ceramic sheet, for example. One end of a coaxial lead wire (hereinafter, called lead wire) 23 (23a, 23b, 23c) for supplying current is connected respectively to each heating element 21 (21a to 21c), the other ends of the lead wires 23 being connected to one end of the connection cable 4.

As described previously, the heating elements 21 (21a to 21c) are coupled thermally to the heat transfer plate 22, in such a manner that the heat generated by the heating elements 21 (21a to 21c) is transmitted to the heat transfer plate 22.

On the other hand, the elastic receiving section 8 is constituted by providing, on an elastic receiving section main unit 8a, a flexible receiving member 24 having a saw section 24a which is able to grasp living-body tissue in conjunction with the heat transfer plate 22 of the heating treatment section 7. By closing the elastic receiving section 8 with respect to the heating treatment section 7 by means of a closing operation of the handle section 20, living-body tissue is grasped flexibly by means of the heat transfer plate 22 of the heating treatment section 7 and the saw section 24a of the elastic receiving section 8. The living-body tissue held between the heat transfer plate 22 and the flexible member 24 is coagulated and cut by the heat of the heat transfer plate 22.

Next, the composition of the electrical circuitry of the heating treatment device according to the present embodiment will be described with reference to FIG. 6.

As shown in FIG. 6, upon the main unit connector 5 of the connection cable 4 of the coagulation and incision forceps 2 being connected to the device main unit 3, information indicating the type of forceps as output by the forceps identifiers 10a of the identifier 10 inside the main unit connector 5, and information for the respective heating elements output by the heating element identifier 10b of the identifier 10, is received by a forceps identifying section 31 in the device main unit 3.

If the forceps identifier 10a and the heating element identifier 10b are electrical resistance elements, the forceps identifying section 31 can recognize and identify the type of forceps and the information for the individual heating elements by measuring the resistance values.

The type of forceps refers to the number and arrangement of heating elements 21 built into the forceps, whilst the information for the individual heating elements refers to the resistance values of the heating elements in a particular environment (for example, 25° C.), in other words, the initial resistance values as an initial characteristics. Consequently, the forceps identifying section 31 comprises an initial characteristics judging device for performing the step of judging the initial characteristics of the heating elements 21 in the present invention, and a judging device for judging the type of forceps connected to the main unit connector 5.

The information received by the forceps identifying section 31 is output to a temperature control and correction section 32. This temperature control and correction section 32 reads in the necessary control resistance value information from a memory 40 forming a memory device, for the respective set temperatures. (level 1 to level 5) of the respective heating elements (21a, 21b, 21c), on the basis of the output information. The memory 40 stores table data as illustrated in FIG. 10 and described hereinafter, which is previously constituted by means of control resistance value information. Therefore, the temperature control and correction section 32 constitutes a table reading device in the present invention.

A heating setting section 33 is electrically connected respectively to the temperature control and correction section 32, an operating section 37 which is an operating device, a foot switch input section 38, and an output power control section 36, and sets the resistance value for controlling the set temperature level being set out of the resistance values for controlling obtained by the temperature control and correction section 32. Therefore, the heating setting section 33 constitutes a modifying device in the present invention for performing a step of correcting the control of the amount of supplied power as performed by the output power control section 36, on the basis of the judgment results of the initial characteristics judgment step described previously, or it constitutes a resistance value data selecting device in the present invention.

An applied power detecting section 34 which is connected electrically to the respective heating elements 21 (21a to 21c) detects the power of the heating elements 21 from the voltage value and current value applied to the heating elements 21, and it outputs information to a resistance value detecting section 35.

The resistance value detecting section 35 calculates the resistance value of the heating element 21 from the voltage value and the current value applied to the heating element 21, as measured by the applied power detecting section 34, and it outputs the calculation result to an output power control section 36. Thereby, the resistance value detecting section 35 constitutes a resistance value detecting circuit in the present invention, or a resistance value detecting device in the present invention.

The output power control section 36 comprises a supplied power generating section 36a which is a power supply device for generating power to be supplied to the heating elements 21, and a power control section 36b which is a control section for controlling the amount of power generated by the supplied power generating section 36a. The output power control section 36 controls the power supply to the respective heating elements 21 (21a to 21c) in such a manner that the resistance values of the heating elements 21 as calculated by the resistance value detecting section 35 are maintained at the resistance values for controlling set by the heating setting section 33. Consequently, the output power control section 36 constitutes a drive circuit for driving the heating elements 21 in the present invention.

Furthermore, the device main unit 3 can be connected to a coagulation and incision forceps 2 having a maximum of four heating elements 21, for example, and in this case, the applied power detecting section 34, the resistance value detecting section 35 and the output power control section 36 function in four channels corresponding respectively to each of these heating elements 21.

Moreover, the heating setting section 33 supplies the output setting information described above to the output power control section 36, in accordance with the temperature setting that is input by operation of the operating section 37, and in accordance with the maximum temperature level output or the set temperature level output that is input by operation of the foot switch 6 (see FIG. 1) via the foot switch input section 38.

Here, the operating section 37 comprises various types of switches, such as a temperature level UP switch 13a (see FIG. 2A), and the like provided on the front face panel 3a described above, and furthermore, the various display LEDs provided on the front face panel 3a constitute a display section 39, for example. Moreover, if an abnormality is detected in the forceps, the output power control section 36 causes the forceps abnormality indicator LED 17a to flash on and off, and causes the buzzer 17c to emit a sound.

The action of the heating treatment device 1 composed in this manner will now be described with reference to FIG. 4 to FIG. 10.

FIG. 7 illustrates the characteristics of a heating element 21, wherein the temperature and the resistance value have a proportional relationship as shown in FIG. 7. Here, as the diagram shows, taking the initial resistance value of the heating element 21 as 25° C., for example, since there is fluctuation in the initial resistance values of the heating elements, as indicated by the symbols 1, 2, 3 in the diagram, even if the device main unit 3 implements control with respect to each of the heating elements 21 (21a to 21c) in such a manner that they have the same temperature setting value, a problem arises in that error occurs in the heating temperature due to each respective heating element.

Therefore, in the present embodiment, as shown in FIG. 9, the heating elements 21 are divided into three groups, indicated by identification group numbers 1 to 3, for example, in accordance with the range of their initial resistance values, and the device main unit 3 recognizes which information, of the aforementioned identification groups 1 to 3, is held by the coagulation and incision forceps 2 connected thereto, and the device main unit 3 performs suitable output control on the basis of this information.

The heating elements 21 (21a to 21c) used on a single coagulation and incision forceps 2 are taken to be of the same identification group.

FIG. 10 is a table showing the relationship between the set temperature and the heating element control resistance value, as stored in the memory 40, and it shows the resistance values for controlling the heating elements in accordance with the differences in the initial characteristics of the heating elements. In this case, the set temperature level is set in steps from level 1 to level 5, as illustrated in FIG. 10, for example.

In other words, in FIG. 10, it is indicated that in order to perform heating to the set level 3, for example, it is necessary to perform control in such a manner that the heating element of group number 1 is maintained at "36 Ω", the heating element of group number 2 is maintained at "35 Ω", and the heating element of group number 3 is maintained at "34 Ω".

In the following description, it is supposed that the forceps identification group classification number for the coagulation and incision forceps 2 (see FIG. 8), and the identification group number of the group classification (see FIG. 9) according to the initial characteristics of the heating element are respectively "C", which indicates a forceps for surgery and the number of element "3", and "2" which indicates a initial resistance value range for the heating elements of 25±0.5 Ω.

Now, the heating treatment device having the composition described above is driven. The following description is centered on the operation of the device main unit 3 of the heating treatment device 1. As shown by the flowchart in FIG. 11, firstly, in the processing in step S1, the device main unit 3 is started up by switching on the power switch 12 (see FIG. 2A), whereupon the procedure advances to step S2.

At the subsequent processing in step S2, it is judged whether or not a coagulation and incision forceps 2 has been connected to the device main unit 3. If it is judged that there is no coagulation and incision forceps 2 connected, then this judgment step is repeated until one is connected. On the other hand, if it is judged that a coagulation and incision forceps 2 has been connected, then the procedure advances to step S3.

In step S3, the device main unit 3 carries out calibration processing. More specifically, if a coagulation and incision forceps 2 has been connected or is being connected to the device main unit 3, in step S71, as illustrated in FIG. 12, the forceps identifying section 31 reads out that the forceps identifier 10a is set to "30 KΩ" and the heating element identifier 10b is set to "20 KΩ", for example, as described previously, and the procedure advances to step S72.

In step S72, the forceps identifying section 31 identifies that the forceps identification group number (see FIG. 8) is "C", and that the heating element initial characteristics identification group number (see FIG. 9) is "2". In this case, due to the fact that the forceps identification group number is "C", the output power control section 36 is set in such a manner that output control is performed for a state where three heating elements are connected. Moreover, by means of the operational control of the output power control section 36, a display is implemented for indicating that a forceps for surgery having three elements is connected. Thereupon, the procedure advances to step S73.

In step S73, the forceps identifying section 31 outputs an identification result to the effect that the initial characteristics identification group number of the heating elements (see FIG. 9) is "2", to the temperature control and correction section 32, whereupon the procedure advances to step S74.

In step S74, in accordance with the identification information thus output indicating that the initial characteristics identification group number of the heating elements (see FIG. 9) is "2", the temperature control and correction section 32 of the device main unit 3 selects and reads out the setting information for a value of "2" from the set temperature—resistance values for controlling heating element (see FIG. 10) stored in the memory 40. The resistance values for controlling heating element, which are read out from the memory 40 in order to control the temperature of the coagulation and incision forceps 2 at the respective set levels, are output from the temperature control and correction section 32 to the heating setting section 33. Thereupon, the procedure advances to step S75.

In step S75, the heating setting section 33 recognizes information indicating that the resistance values for controlling heating element for the respective setting levels are "level 1=31 Ω, level 2=33 Ω, level 3=35 Ω, level 4=37 Ω, level 5=39 Ω". When the calibration processing of this kind has been completed, the procedure advances to step S4.

Returning to FIG. 11, in step S4, the device main unit 3 executes heating level setting processing. More specifically, the heating level for the heating elements 21 in the device main unit 3 is set to a desired level from level 1 to level 5, as illustrated in FIG. 10, by means of depressing the temperature level UP switch 13a and/or the temperature level DOWN switch 13b (see FIG. 2A in both cases) located on the operating section 37 of the device main unit 3. In this case, according to the present embodiment, for example, it is set to heating level 4.

Upon the heating level setting operation in the operating section 37 being ended, in step S81, as illustrated in FIG. 13, the heating setting section 33 of the device main unit 3 recognizes a voltage signal indicating that the heating elements 21 are to be controlled to the resistance value "level 4=37 Ω", out of the resistance values for controlling heating element "level 1=31 Ω, level 2=33 Ω, level 3=35 Ω, level 4=37 Ω, level 5=39 Ω", whereupon the procedure advances to step S82.

In step S82, the heating setting section 33 of the device main unit 3 outputs to the output power control section 36 a voltage signal indicating that the heating elements 21 are to be controlled to a resistance value of "level 4=37 Ω", out of the resistance values for controlling heating element "level 1=31Ω, level 2=33 Ω, level 3=35 Ω, level 4=37 Ω, level 5=39 Ω".

Thereupon, the procedure advances to step S5.

Returning to FIG. 11, in step S5, the device main unit 3 carries out heating control processing by means of the foot switch (F. SW) 6 being turned on.

More specifically, if the set temperature level output switch 6b of the foot switch 6 (see FIG. 1 in both cases) is depressed in a state where the heating level has been set by the processing in step S4 described above, then the foot switch input section 38 outputs an on signal to the output power control selection 36. Thereupon, the output power control section 36 performs control in such a manner that power is supplied to the heating element 21 so as to maintain the heating elements 21 at "37 Ω".

Moreover, if the maximum temperature level output switch 6a of the foot switch 6 (see FIG. 1 in both cases) is depressed, a signal indicating heating to level 5, which is the maximum level, is output to the heating setting section 33, and the heating setting section 33 to which this signal is sent in turn outputs a voltage signal to the output power control section 36 indicating that the heating element 21 is to be controlled to a resistance value of "level 5=39 Ω", rather than the setting level up to that time. Moreover, at the same time, the foot switch input section 38 receives a signal from the maximum temperature level output switch 6a and supplies an on signal to the output power control section 36, and the output power control section 36 performs control in such a manner that power is supplied to the heating elements 21 in such a manner that the heating elements 21 maintain "39 Ω", in other words, the maximum heating temperature level.

Consequently, according to the heating treatment device illustrated by the first embodiment of the present invention and the heating operating control method for the same, the device main unit 3 is able to reduce error in controlling the temperature of the heating elements 21, by performing temperature control whilst correcting for the effect of disparity in the initial resistance value of the heating elements. Moreover, the heating elements are classified into a number of groups according to the range of variation of the initial resistance values thereof, and by selecting heating elements of the same group from these classified groups, and using them in the same coagulation and incision forceps, then it is possible to reduce the identifiers.

Second Embodiment

Figure 14:
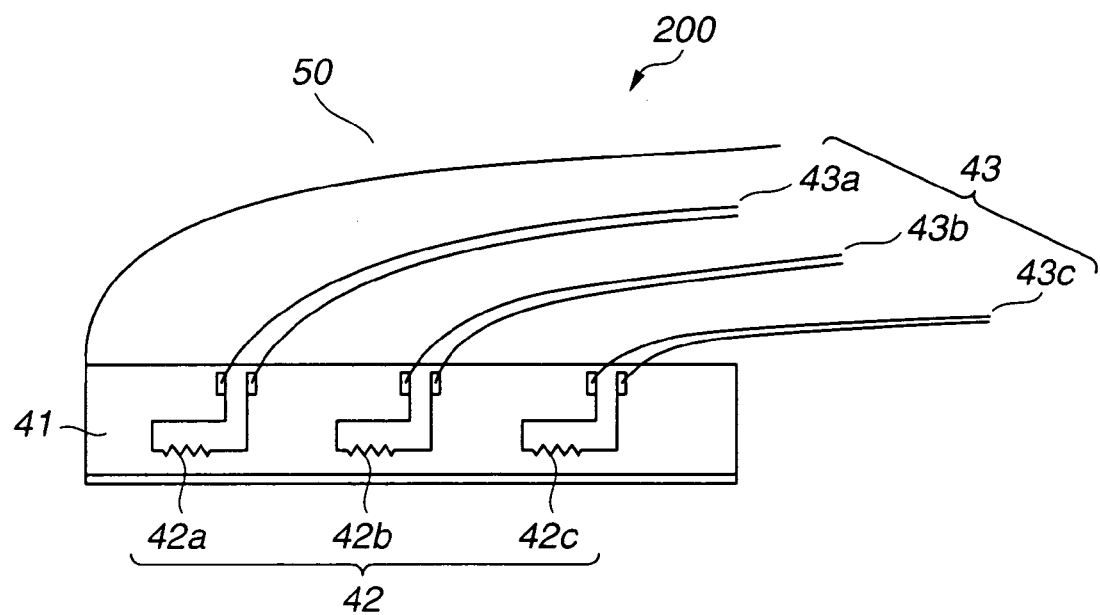
FIG. 14 is a diagram showing an overview of the composition of a heating treatment section of a heating treatment device illustrating a second embodiment of the present invention.

FIG. 14 to FIG. 16 relate to a second embodiment of a heating treatment device and a heating operating control method for the same according to the present invention, wherein FIG. 14 is a diagram showing an overview of the composition of a heating treatment device illustrating a second embodiment of the present invention; FIG. 15 is a diagram showing a table indicating group classifications according to initial characteristics of the heating patterns of the heating treatment section in FIG. 14; and FIG. 16 is a diagram showing a table indicating heating pattern identification group numbers according to the initial characteristics of the heating patterns of the heating treatment section in FIG. 14. The heating treatment device according to the present embodiment is a modification of the first embodiment described above, and constituent members which are the same as those in the device of the first embodiment described above are labeled with the same reference numerals and description thereof is omitted here only the differing portions being described.

The heating treatment device 200 illustrating a second embodiment of the present invention comprises, as the principal parts thereof, a coagulation and incision forceps 50, and a device main unit 3 (see FIG. 1), as indicated in the first embodiment described above. As shown in FIG. 14, the coagulation and incision forceps 50 has a treatment section 9 for grasping and treatment living-body tissue (see FIG. 1), and the treatment section 9 comprises, as the principal parts thereof, a heating treatment section 41 in which a plurality of heating patterns 42 (42a to 42c) which are heaters are formed, and an elastic receiving section 8 which can be placed in contact with, and separated from, the heating treatment section 41 (see FIG. 1).

One end of a lead wire 43 (43a, 43b, 43c) for supplying current is connected respectively to the aforementioned heating patterns 42a to 42c, and the other ends of the lead wires 43 are connected to one end of a connection cable 4 (see FIG. 1). As described above, a main unit connector 5 (see FIG. 1) is provided on the other end of the connection cable 4.

The respective heating patterns 42a to 42c formed on the heating treatment section 41 each have different initial characteristics. Therefore, heating pattern identifiers 50b-1, 50b-2, 50b-3 (not illustrated) for the purpose of carrying out calibration processing, are provided in the main unit connector 5, in correspondence to each of the respective heating patterns 42a to 42c. The heating pattern identifiers 50b-1, 50b-2, 50b-3 may also be provided in the heating treatment section 41.

Furthermore, in the heating treatment device 200 according to the present embodiment, a group classification according to the initial characteristics of the heating patterns, as illustrated in FIG. 15, is employed, and identification group numbers for the heating patterns 42 are indicated in accordance with the initial characteristics of the heating patterns, as shown in FIG. 16. Furthermore, the resistance values for controlling the heating patterns according to change in the initial characteristics of the heating patterns 42a to 42c are taken as the same set temperature—resistance values for controlling heating element as those described in relation to the first embodiment and illustrated in FIG. 10.

By means of the aforementioned composition, in a heating treatment device 200 according to the present embodiment, it is possible to reduce temperature irregularity in the heating treatment section 41, by performing output control in accordance with the initial characteristics of the respective heating patterns 42a to 42c. The rest of the composition is approximately similar to that of the first embodiment described above.

Next, the action of the heating treatment device 200 illustrating a second embodiment as composed above shall be described with reference to FIG. 11 to FIG. 16. The flowchart shown in FIG. 11 to FIG. 13 indicates the basic control operation procedure performed in the device main unit 3 of the heating treatment device 200 according to the present invention, and it is also employed in the present embodiment.

Now, it is supposed that the heating treatment device 200 composed as described above is driven. The following description is centered on the operation of the device main unit 3 of the heating treatment device 1. As shown by the flowchart in FIG. 11, firstly, in the processing in step S1, the device main unit 3 (see FIG. 1) is started up by means of the power switch 12 (see FIG. 2A) being turned on, and the procedure advances to step S2.

In the subsequent processing in step S2, it is judged whether or not a coagulation and incision forceps 50 is connected to the device main unit 3. If it is judged that no coagulation and incision forceps 50 has been connected, then this judgment processing is repeated until one is connected. If it is judged that a coagulation and incision forceps 50 is connected, then the procedure advances to step S3.

In step S3, the device main unit 3 executes calibration processing. More specifically, if a coagulation and incision forceps 50 has been connected or is being connected to the device main unit 3, in step S71, as illustrated in FIG. 12, the forceps identifying section 31 (see FIG. 6) reads out, for example, that the heating pattern identifier 51*b*-1 is set to "20 K$\Omega$", the heating pattern identifier 51*b*-2 is set to "10 K$\Omega$" and the heating pattern identifier 51*b*-3 is set to "30 K$\Omega$", whereupon the procedure advances to step S72.

In step S72, the forceps identifying section 31 identifies that the initial characteristic identification group numbers for the heating patterns (see FIG. 16), are respectively "2", "1", "3", with respect to the heating pattern identifiers 50*b*-1, 50*b*-2, 50*b*-3. Thereupon, the procedure advances to step S73.

In step S73, the forceps identifying section 31 outputs the identification results for the initial characteristics identification group numbers (see FIG. 16) of the heating patterns, to the temperature control and correction section 32, whereupon the procedure advances to step S74.

In step S74, in accordance with the identification information thus output indicating that the initial characteristics identification group numbers for the heating patterns are "2", "1" and "3", the temperature control and correction section 32 of the device main unit 3 selects and reads out respective setting information for each of the heating patterns, from the set temperature—resistance values for controlling heating element (see FIG. 10) stored in a memory 40 (see FIG. 6). The heating pattern resistance values for controlling required to control the temperature of the coagulation and incision of forceps 50 to the respective set levels, as read out from the memory 40, are output from the temperature control and correction section 32 to the heating setting section 33 (in both cases, see FIG. 6). Thereupon, the procedure advances to step S75.

In step S75, the heating setting section 33 identifies the heating pattern resistance values for controlling each set level to be "level 1=31 $\Omega$, level 2=33 $\Omega$, level 3=35 $\Omega$, level 4=37 $\Omega$, level 5=39 $\Omega$," for heating pattern 42*a*, "level 1=32 $\Omega$, level 2=34 $\Omega$, level 3=36 $\Omega$, level 4=38 $\Omega$, level 5=40 $\Omega$," for heating pattern 42*b*, and "level 1=30 $\Omega$, level 2=32 $\Omega$, level 3=34 $\Omega$, level 4=36 $\Omega$, level 5=38 $\Omega$," for heating pattern 42*c*. When the calibration processing of this kind has been completed, the procedure advances to step S4.

Returning to FIG. 11, in step S4, the device main unit 3 performs heating level setting processing. More specifically, the heating level of the heating patterns 42 is set to a desired level from level 1 to level 5, as illustrated in FIG. 10, by means of pressing the temperature level UP switch 13*a* and/or the temperature level DOWN switch 13*b* (see FIG. 2A in both cases) of the operating section 37 on the device main unit 3. In this case, in the present embodiment, the heating level is set to level 4, for example.

Upon the heating level setting operation in the operating section 37 being ended, in step S81, as illustrated in FIG. 13, the heating setting section 33 of the device main unit 3 recognizes a voltage signal indicating that the heating patterns 42 are to be controlled to a resistance value of "level 4=37 $\Omega$", out of the heating pattern resistance values for controlling "level 1=31 $\Omega$, level 2=33 $\Omega$, level 3=35 $\Omega$, level 4=37 $\Omega$, level 5=39 $\Omega$" in the case of heating pattern 42*a*, a resistance value of "level 4=38 $\Omega$" out of the heating pattern resistance values for controlling "level 1=32 $\Omega$, level 2=34 $\Omega$, level 3=36 $\Omega$, level 4=38 $\Omega$, level 5=40 $\Omega$" in the case of heating pattern 42*b*, and a resistance value of "level 4=36 $\Omega$" out of the heating pattern resistance values for controlling "level 1=30 $\Omega$, level 2=32 $\Omega$, level 3=34 $\Omega$, level 4=36 $\Omega$, level 5=38 $\Omega$" in the case of heating pattern 42*c*. The procedure then advances to step S82. In step S82, the heating setting section 33 of the device main unit 3 outputs voltage signals whereby the heating patterns 42 are controlled to the aforementioned resistance values, to the output power control section 36 (see FIG. 6). Thereupon, the procedure advances to step S5.

Returning to FIG. 11, in step S5, the device main unit 3 performs heating control processing by means of the foot switch (F. SW) 6 (see FIG. 1) being turned on.

More specifically, if the set temperature level output switch 6*b* of the foot switch 6 (in both cases see FIG. 1) is depressed when the heating level has been set by the processing in step S4 described above, the foot switch input section 38 (see FIG. 6) outputs an on signal to the output power control section 36. Thereupon, the output power control section 36 performs control in such a manner that power is supplied to the heating patterns 42 (42*a* to 42*c*) in so that the heating patterns 42*a*, 42*b*, 42*c* are maintained at "37 $\Omega$", "38 $\Omega$" and "36 $\Omega$" respectively.

Moreover, if the maximum temperature level output switch 6*a* of the foot switch 6 (in both cases see FIG. 1) is depressed, a signal indicating heating to level 5, which is the maximum level, is output to the heating setting section 33, and the heating setting section 33 to which this signal is output in turn outputs a voltage signal indicating that the heating elements 42 are to be controlled to resistance values of "level 5" (42*a*=39 $\Omega$, 42*b*=40 $\Omega$, 42*c*=38 $\Omega$), rather than the setting level up to that time, to the output power control section 36. Moreover, at the same time, the foot switch input section 38, receiving the signal from the maximum temperature level output switch 6*a*, outputs an on signal to the output power control section 36, and the output power control section 36 performs control in such a manner that power is supplied to the heating elements 42 so that the heating elements 42 maintain the maximum heating temperature level.

In this way, according to the heating treatment device and heating operation control method for the same according to the second embodiment of the present invention, in addition to obtaining merits similar to those of the heating treatment device and heating operation control method for the same according to the first embodiment described above, a merit is also obtained in that, by increasing the heating pattern identifiers to a plurality of elements, then even if heating patterns having mutually different initial heating characteristics are formed in an integral fashion, it is possible to reduce the temperature control differential between the heating patterns 42.

Third Embodiment

Figure 18:
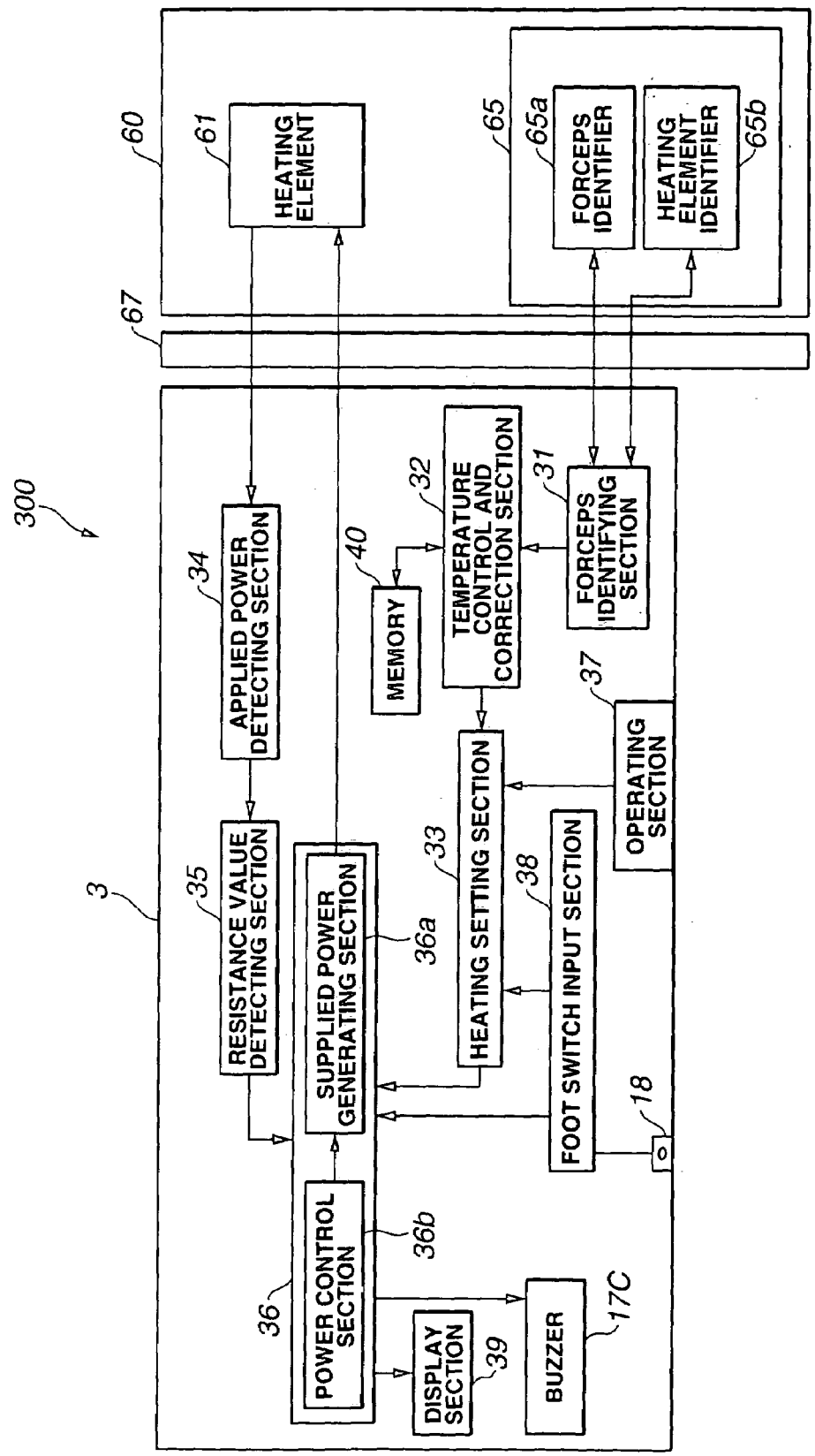
FIG. 18 is a block diagram showing the composition of the electrical circuitry of the heating treatment device illustrating a third embodiment according to the present invention.

FIG. 17 to FIG. 18 relate to a third embodiment of a heating treatment device and a heating operation control method for the same according to the present invention, wherein FIG. 17 is a diagram showing an overview of the composition of a heating treatment section of a heating treatment device illustrating a third embodiment of the present invention and FIG. 18 is a block diagram showing the composition of the electrical circuitry of the heating treatment device illustrating a third embodiment according to the present invention. The device according to the embodiment illustrated in FIG. 17 and FIG. 18 is a modification of the first embodiment described above, and constituent parts that are the same as the device according to the first embodiment are labeled with the same reference numerals, further description thereof is omitted here and only the differing portions are described here.

As illustrated in FIG. 17 and FIG. 18, a characteristic feature of a heating treatment device 300 illustrating a third embodiment of the present invention lies in that the identifier 10 according to the first embodiment described above is provided inside a coagulation and incision forceps 60 as an identifier 65, instead of inside a main unit connector 67.

The identifier 65 which is an identification device comprises, as the principal parts thereof, a forceps identifier 65a which indicates the type of forceps, and a heating element identifier 65b which holds information for individual heating elements.

The identifier 65 is, for example, an electrical resistance pattern formed on a flexible substrate 66, and the heating elements 61 (61a to 61c), which are heaters, are, for example, thin sheet resistors formed on a ceramic plate. Wiring (not illustrated) for passing current to these heating elements 61 (61a to 61c) is formed on the flexible substrate 66, and the flexible substrate 66 is connected to one end of a connection cable 63, which has a main unit connector 67 provided on the other end thereof.

The remaining composition and actions are similar to those of the first embodiment described above.

In this way, according to the heating treatment device and the heating operation control method for the same according to the third embodiment of the present invention, in addition to obtaining merits approximately similar to those of the heating treatment device and the heating operation control method for the same according to the first embodiment described above, by providing the identifier 65 in the flexible substrate 66 inside the coagulation and incision forceps 60, it is possible to incorporate the identifier more readily than in a case where it is disposed in the main unit connector.

Fourth Embodiment

Figure 19:
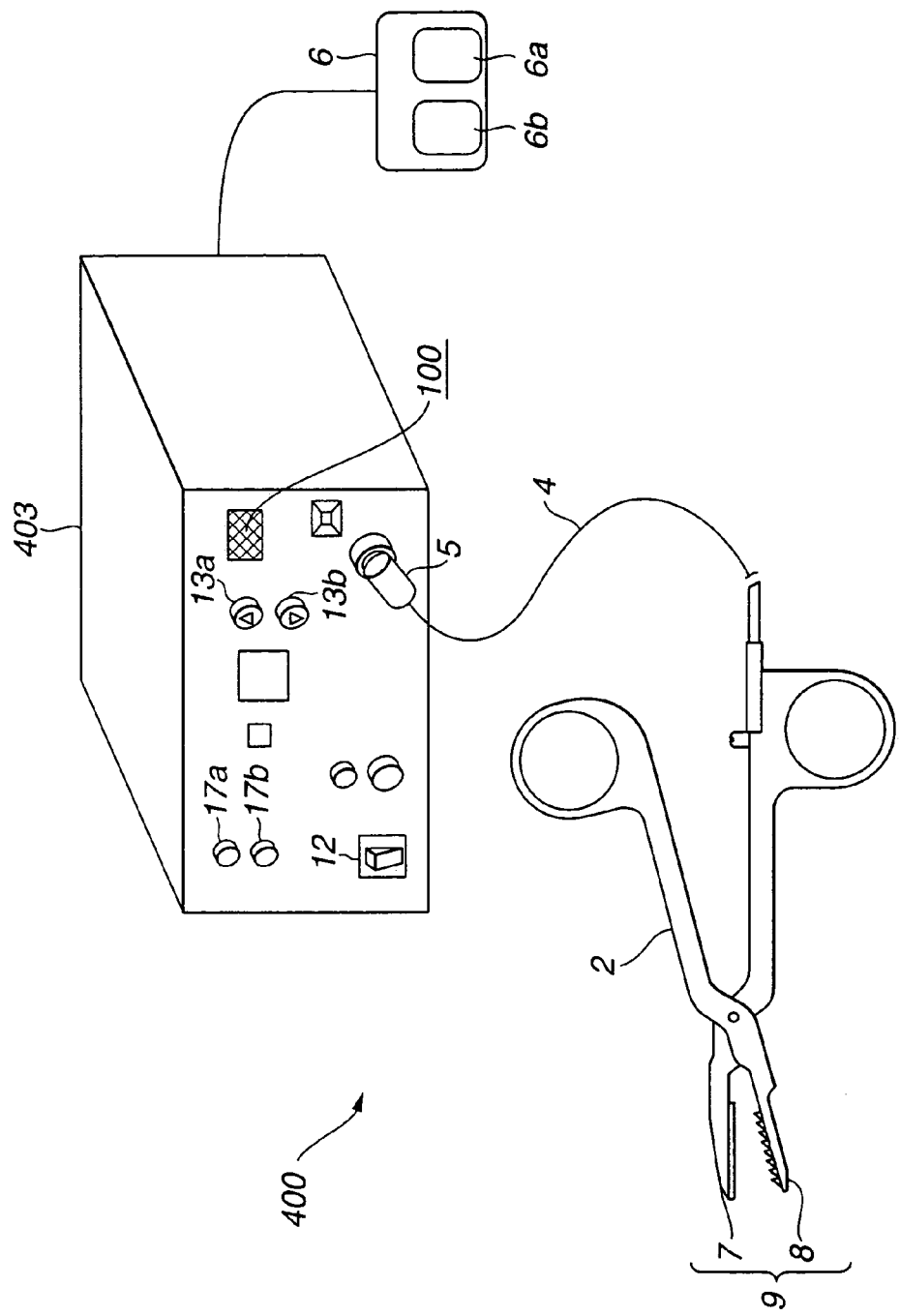
FIG. 19 is a perspective view of a heating treatment device illustrating a fourth embodiment according to the present invention.
Figure 20:
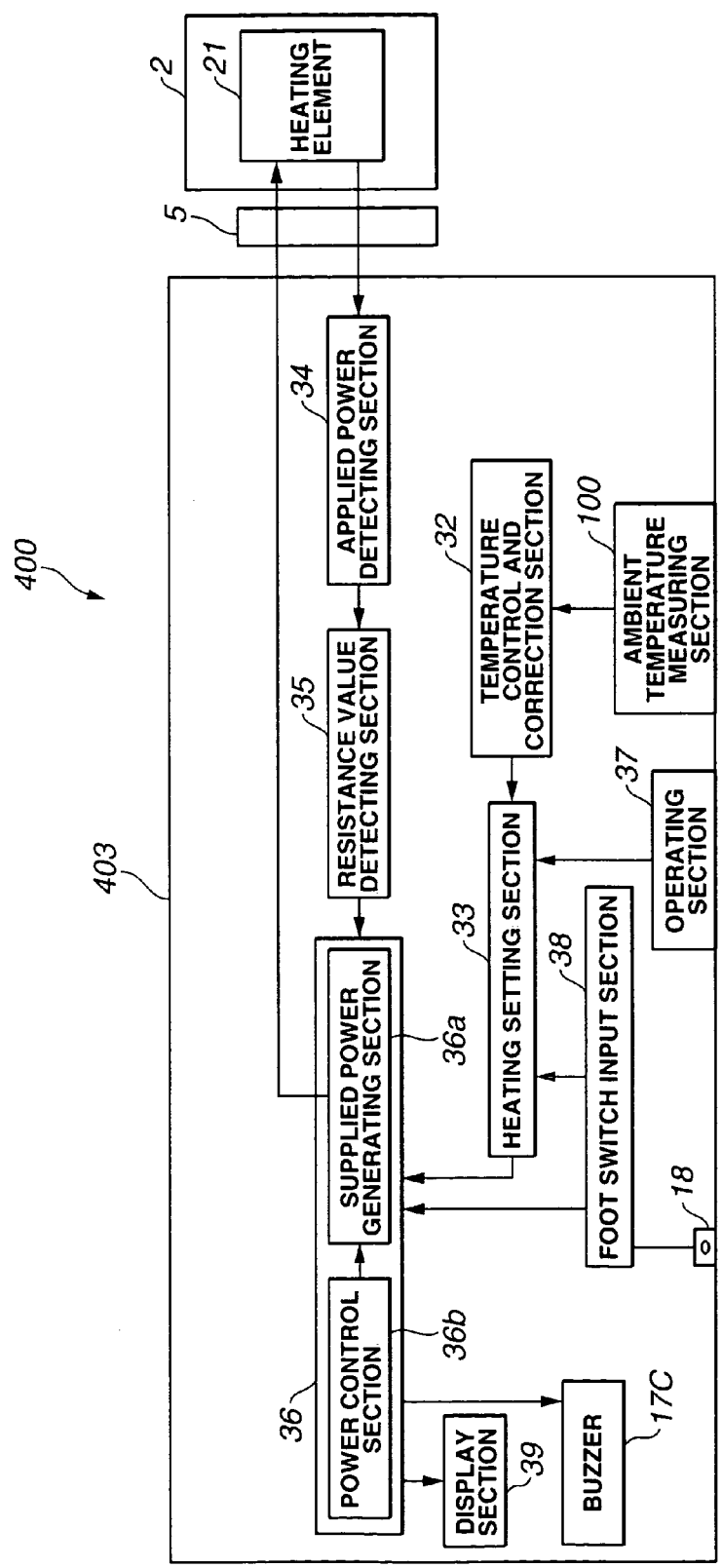
FIG. 20 is a block diagram showing the composition of the electrical circuitry of the heating treatment device in FIG. 19.
Figures 21, 22:
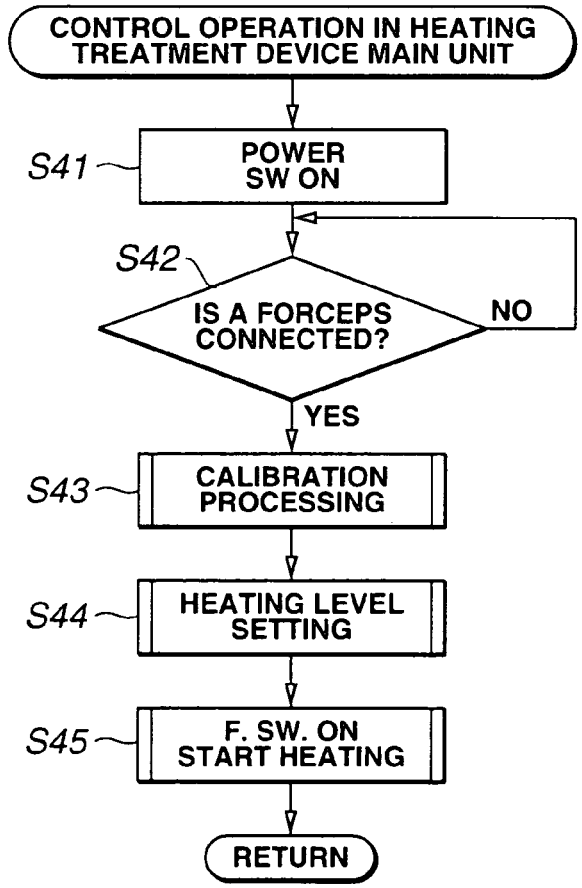
FIG. 21 is a diagram showing a table indicating the relationship between set temperatures and resistance values for controlling heating element in FIG. 20.
FIG. 22 is a flowchart showing the operational procedure of the device main unit of the heating treatment device in FIG. 19.

FIG. 19 to FIG. 24 relate to a fourth embodiment of a heating treatment device and a heating operation control method for the same according to the present invention, wherein FIG. 19 is a perspective view of a heating treatment device illustrating a fourth embodiment according to the present invention; FIG. 20 is a block diagram showing the composition of the electrical circuitry of the heating treatment device in FIG. 19; FIG. 21 is a diagram showing a table indicating the relationship between set temperatures and resistance values for controlling heating element; FIG. 22 is a flowchart showing the operational procedure of the device main unit of the heating treatment device in FIG. 19; FIG. 23 is a flowchart illustrating the calibration processing in FIG. 22; and FIG. 24 is a flowchart illustrating the heating level setting in FIG. 22.

The heating treatment device according to the present embodiment illustrated in FIG. 19 and FIG. 20 is a modification of the first embodiment described above, and constituent parts thereof that are the same as those of the device according to the first embodiment described above are labeled with similar reference numerals, description thereof being omitted and only differing portions being described here.

The characteristic feature of the heating treatment device 400 according to the present embodiment lies in that an ambient temperature measuring section 100, which is an environmental temperature measuring device, is provided in the composition of the heating treatment device 1 according to the first embodiment described above and illustrated in FIG. 1.

As shown in FIG. 19, the heating treatment device 400 illustrating a fourth embodiment of the present invention comprises the ambient temperature measuring section 100 provided in a prescribed position of the front face panel 403a of the device main unit 403. This ambient temperature measuring section 100 is constituted, for example, by means of a temperature sensor which converts a measured temperature into an electrical signal.

As illustrated in FIG. 20, the ambient temperature measuring section 100 measures the temperature in the vicinity of the device main unit 403, and supplies the measured temperature information to the temperature control and correction section 32. This measurement information may be in the form of a voltage value, for example.

An applied power detecting section 34 detects the power of the heating elements 21 from the voltage value and current value applied to the heating elements 21, and outputs the power of the heating elements 21 to a resistance value detecting section 35.

The resistance value detecting section 35 calculates the resistance value of the heating elements 21 from the voltage value and current value applied to the heating elements 21 which have been detected in the applied power detecting section 34, and the resistance value detection section 35 outputs the calculation result to a temperature control and correction section 32 and an output power control section 36.

Using the temperature information from the ambient temperature measuring section 100 and the resistance value information from the resistance value detecting section 35, the temperature control and correction section 32 performs calibration processing for calculating the required resistance values for controlling each set temperature (level 1 to level 5) and for each of the heating elements 21 (21a to 21c), and the temperature control and correction section 32 outputs the calculation results to the heating setting section 33. Therefore, the temperature control and correction section 32 constitutes a temperature correcting device in the present invention.

The heating setting section 33 sets the control resistance value the specified temperature level from the resistance values for controlling calculated by the temperature control and correction section 32.

The output power control section 36 controls the supply of electrical power to the respective heating elements 21 (21a to 21c), in such a manner that the resistance value calculated by the resistance value detecting section 35 is maintained to be equal to the resistance value set by the heating setting section 33.

Moreover, the device main unit 403 can be connected to a coagulation and incision forceps having a maximum of four heating elements 21, for example, and in this case, the applied power detecting section 34, the resistance value detecting section 35 and the output power control section 36 function in four channels corresponding respectively to each of these heating elements 21.

Furthermore, the heating setting section 33 outputs the aforementioned output setting information to the output power control section 36, in accordance with the temperature setting input by operation of the operating section 37, and in accordance with the maximum temperature level output or set temperature level output setting input by operation of the foot switch 6 (see FIG. 19), by means of the foot switch input section 38.

Here, the operating section 37 prefers to various types of switches, such as a temperature level UP switch 13a, or the like, provided on the front face panel 403a as described above, and the various types of display LED described above which are provided on the front face panel 403a constitute a display section 39. Moreover, if an abnormality is detected in the forceps, the output power control section 36 causes the forceps abnormality indicator LED 17a to flash on and off and also causes the buzzer 17c to emit a sound.

The remainder of the composition is approximately the same as that of the heating treatment device of the first embodiment described above.

Next, the actual operation of the heating treatment device 400 according to the present embodiment will be described with reference to FIG. 19 to FIG. 24. The flowchart shown in FIG. 22 illustrates a basic control operation procedure for the device main unit 403 of the heating treatment device 400 according to the present invention, and it may also be applied to the present embodiment.

Now, it is supposed that the heating treatment device having the composition described above is driven. The following description is centered on the operation of the device main unit 403 of the heating treatment device 400. As shown by the flowchart in FIG. 22, firstly, in the processing in step S41, the device main unit 403 is started up by means of the power switch 12 (see FIG. 19) being switched on, whereupon the procedure advances to step S42.

In the subsequent processing in step S42, it is judged whether or not a coagulation and incision forceps 2 has been connected to the device main unit 403. If it is judged that no coagulation and incision forceps 2 has been connected, this judgment processing is repeated until one is connected. On the other hand, if it is judged that a coagulation and incision forceps 2 is connected, the procedure advances to step S43.

In step S43, the device main unit 403 performs calibration processing. More specifically, as shown in FIG. 23, if a coagulation and incision forceps 2 has been connected or is being connected to the device main unit 403, then firstly, in step S51, the resistance value detecting section 35 of the device main unit 403 detects the respective resistance values of the heating elements 21 (21a to 21c), on the basis of the information from the applied power detecting section 34, and outputs the same to the temperature control and correction section 32. In the present embodiment, the resistance values of the heating elements 21 are taken to be, for example, "23 Ω" for heating element 21a, "25 Ω" for heating element 21b, and "27 Ω" for heating element 21c. Thereupon, the procedure advances to step S52.

In step S52, the ambient temperature measuring section 100 which is disposed externally to the device main unit 403 measures the ambient temperature (the environmental temperature of the heating section) at the time that the resistance value detecting section 35 detects the resistance values, and the ambient temperature measuring section 100 outputs a voltage signal for the same to the temperature control and correction section 32. In this case, it is supposed, for example, that the ambient temperature was 25° C. This ambient temperature is taken as the temperature information for the time at which the resistance values of the respective heating elements 21 (21a to 21c) were measured. Thereupon, the procedure advances to step S53.

In step S53, in order to control the respective heating elements 21 (21a to 21c) in accordance with the set temperature, the temperature control and correction section 32 of the device main unit 403 calculates resistance values for controlling the heating elements, from the resistance values of the heating elements 21 detected in step S51 and the aforementioned ambient temperature measured in step S52. In this case, if the value, in other words, the ambient temperature, that is output to the temperature control and correction section 32 is 25° C., the resistance values for controlling are calculated using characteristics information for the respective heating elements 21 (21a to 21c) which indicate "23 Ω" for heating element 21a, "25 Ω" for heating element 21b and "27 Ω" for heating element 21c.

The calculation results for the resistance values for controlling heating element, as calculated by the temperature control and correction section 32 in this manner, are as illustrated in FIG. 21, wherein the values are "level 1=30 Ω, level 2=32 Ω, level 3=34 Ω, level 4=36 Ω, level 5=38 Ω" for the heating element 21a, "level 1=31 Ω, level 2=33 Ω, level 3=35 Ω, level 4=37 Ω, level 5=39 Ω" for the heating element 21b, and "level 1=32 Ω, level 2=34 Ω, level 3=36 Ω, level 4=38 Ω, level 5=40 Ω" for the heating element 21c. After calculating the resistance values for controlling the heating elements, the procedure advances to step S54.

In step S54, the resistance values for controlling the heating elements as calculated in step S53 are output from the temperature control and correction section 32 of the device main unit 403 to the heating setting section 33, whereupon the procedure advances to step S55.

In step S55, the heating setting section 33 of the device main unit 403 recognizes that the resistance values for controlling heating element for the respective setting levels are "level 1=30 Ω, level 2=32 Ω, level 3=34 Ω, level 4=36 Ω, level 5=38 Ω" for heating element 21a, "level 1=31 Ω, level 2=33 Ω, level 3=35 Ω, level 4=37 Ω, level 5=39 Ω" for heating element 21b, and "level 1=32 Ω, level 2=34 Ω, level 3=36 Ω, level 4=38 Ω, level 5=40 Ω" for heating element 21c. The procedure then returns.

Returning to FIG. 22, when the calibration processing in step S43 has been completed in this fashion, the device main unit 403 of the heating treatment device 400 performs heating level setting in the subsequent processing in step S44.

More specifically, as illustrated in FIG. 24, firstly, in step S61, the device main unit 403 sets the heating level of the heating elements 21 to a desired level from level 1 to level 5, by means of the temperature level UP switch 13a and/or the temperature level DOWN switch 13b (see FIG. 19 in both cases) on the operating section 37 (see FIG. 20) being depressed. In this case, in the present embodiment, it is supposed that the heating level is set to level 2.

In this, upon a heating level setting operation being ended in the operating section 37, the heating setting section 33 identifies output control signals, which are voltage signals, indicating that the heating elements 21 are to be controlled to a value of "level 2=32 Ω" out of the resistance values for controlling heating element "level 1=30 Ω, level 2=32 Ω, level 3=34 Ω, level 4=36 Ω, level 5=38 Ω" in the case of the heating element 21a, to a value of "level 2=33 Ω" out of the heating element control resistance value "level 1=31 Ω, level 2=33 Ω, level 3=35 Ω, level 4=37 Ω, level 5=39 Ω" in the case of the heating element 21b, and to a value of "level 2=34 Ω" out of the resistance values for controlling heating element "level 1=32 Ω, level 2=34 Ω, level 3=36 Ω, level 4=38 Ω, level 5=40 Ω" in the case of the heating element 21c. The procedure then advances to step S62.

In step S62, the heating setting section 33 of the device main unit 403 outputs the aforementioned output control signal recognized in step S61, to the output power control section 36. Thereupon, the procedure returns.

Returning to FIG. 22, in step S45, the device main unit 403 performs heating control processing by means of the foot switch (F. SW) 6 being turned on.

More specifically, if the set temperature level output switch 6b of the foot switch 6 (see FIG. 19 both cases) is depressed when a heating level has been set by the processing in step S44, the foot switch input section 38 outputs an on signal to the output power control section 36. Thereupon, the output power control section 36 performs control in such a manner that power is supplied to the heating elements 21 (21*a* to 21*c*) so that values of "32 Ω", "33 Ω", "34 Ω" are respectively maintained by the heating elements 21*a* to 21*c*.

Moreover, if the maximum temperature level output switch 6*a* of the foot switch 6 (in both cases, see FIG. 19) is depressed, a signal indicating heating to level 5, which is the maximum level, is supplied to the heating setting section 33, and upon receiving this signal, the heating setting section 33 supplies a voltage signal whereby the heating elements 21 are controlled to "level 5" resistance values (21*a*=38 Ω, 21*b*=39 Ω, 21*c*=40 Ω), rather than the set level up to that time, to the output power control section 36. Moreover, at the same time, the foot switch input section 38 receives a signal from the maximum temperature level output switch 6*a* and supplies an on signal to the output power control section 36, and the output power control section 36 performs control in such a manner that power is supplied to the heating elements 21 so that they maintain the maximum heating temperature level.

In this way, according to the heating treatment device and the heating operation control method for the same according to the fourth embodiment of the present invention, in addition to obtaining merits approximately similar to those of the heating treatment device and heating operation control method for the same according to the first embodiment described above, by performing calibration processing for individual heating elements, it is possible to obtain a highly accurate heating temperature, or more specifically, a heating temperature in which there is no error from the set temperature. Furthermore, by using the ambient temperature when carrying out calibration processing, it is not necessary to provide identification information for the coagulation and incision forceps, and hence costs relating to the coagulation and incision forceps can be reduced.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A heating treatment apparatus comprising:
    a plurality of treatment tools each having a heater for generating heat for treating living-body tissues;
    a driving device having a connector receiving section composed in such a manner that at least one of the plurality of treatment tools can be attached to or detached therefrom, selectively, and a driving circuit for driving the heater by supplying electrical power thereto to one or more temperature levels;
    a resistance value detecting circuit for detecting a resistance value of the heater on the basis of the electrical power supplied to the heater by the driving circuit;
    a control section for controlling the supply of electrical power by the driving circuit, on the basis of the detection results of the resistance value detecting circuit;
    an identifying device provided respectively for each one of the plurality of treatment tools;
    a judging device for judging at least one treatment tool connected to the connector receiving section, on the basis of the identifying device; and
    a heating setting device for setting a resistance value for each temperature level, respectively, for controlling the driving circuit on the basis of the judgment results of the judging device.

2. The heating treatment apparatus according to claim 1, wherein the identifying device comprises a treatment tool identifier for indicating the type of the treatment tool and a heating element identifier holding respective initial resistance value information for individual heaters.

3. The heating treatment apparatus according to claim 1, wherein the treatment tool comprises:
    a treatment section for grasping and treating living-body tissues; and
    a connector which can be freely attached to and detached from the connector receiving section of the driving device;
    wherein the identifying device is provided in the treatment section or the connector.

4. The heating treatment apparatus according to claim 1, wherein the judging device judges the type of the treatment tool and the initial resistance value thereof.

5. A heating treatment apparatus comprising:
    a plurality of treatment tools each having a heater for generating heat for treating living-body tissues;
    a driving device having a connector receiving section composed in such a manner that at least one of the plurality of treatment tools can be freely attached to or detached therefrom, selectively, and a power supply device for supplying electrical power to the heater while controlling the amount of heat generated by the heater to one or more temperature levels;
    a resistance value detecting device for detecting a resistance value of the heater on the basis of the electrical power supplied by the power supply device;
    a memory device for storing a plurality of resistance value tables corresponding to changes in the heating temperatures of the heater, respectively in association with a plurality of treatment tools;
    a judging device for judging at least one treatment tool connected to the connector receiving section;
    a table reading device for selectively reading out resistance value data from the plurality of resistance value tables stored in the memory device, on the basis of the judgment results of the judging device;
    a heating setting device for setting a resistance value for each temperature level, respectively, for controlling the power supply device on the basis of judgment results from the judging device;
    an operating device for setting the temperature level of the heater; and
    a control section for controlling the supply of power to the heater by the power supply device, on the basis of the resistance value set by the heating setting device corresponding to the set temperature level set by the operating device and the detection results of the resistance value detecting device;
    wherein the heating setting device sets the resistance value for each temperature level, respectively, on the basis of the resistance value data read out from the plurality of resistance value tables.

6. The heating treatment apparatus according to claim 5, wherein the treatment tool comprises:
    a treatment section for grasping and treating living-body tissues; and
    a connector which can be freely attached to and detached from the connector receiving section of the driving device;
    wherein the judging device judges the type of the treatment tool and an initial resistance value thereof.

7. A heating treatment apparatus comprising:

a treatment tool having a heater for generating heat for treating living-body tissues;

a resistance value detecting device for detecting the resistance value of the heater, on the basis of the electrical power supplied to the heater;

an temperature measuring device for measuring the ambient temperature in a vicinity of the heating treatment apparatus nearly simultaneously to the resistance value detecting device detecting the resistance value of the heater;

a temperature correcting device for calculating a required resistance value for each temperature level on the basis of the detection results detected by the resistance value detecting device and the measurement results measured by the temperature measuring device;

a heating setting device for setting a control resistance value for a specific temperature level, said control resistance value is selected from said required resistance value for each temperature level calculated by the temperature correcting device; and an output power control section for controlling the electrical power supplied to the heater of the treatment tool, on the basis of the control resistance value set by the heating setting device.

* * * * *